United States Patent [19]

Evans

[11] Patent Number: 5,161,524
[45] Date of Patent: Nov. 10, 1992

[54] DOSAGE INHALATOR WITH AIR FLOW VELOCITY REGULATING MEANS

[75] Inventor: Rix E. Evans, Wendell, N.C.

[73] Assignee: Glaxo Inc., Research Triangle Park, N.C.

[21] Appl. No.: 739,905

[22] Filed: Aug. 2, 1991

[51] Int. Cl.⁵ .................. A61M 15/00; A61M 16/00; B05D 7/14; B65D 83/06
[52] U.S. Cl. .......................... 128/203.15; 128/200.24; 128/203.12; 128/203.23
[58] Field of Search .................. 128/200.14, 200.18, 128/200.21, 200.22, 203.12, 203.15, 203.14, 203.19, 203.23, 203.24, 200.24

[56] References Cited

U.S. PATENT DOCUMENTS

| | | |
|---|---|---|
| 1,309,597 | 7/1919 | Parker . |
| 1,431,177 | 10/1922 | Palmer . |
| 2,470,296 | 4/1948 | Fields . |
| 2,470,298 | 2/1949 | Fields . |
| 2,503,732 | 1/1949 | Heisterkamp . |
| 2,517,482 | 4/1949 | Hall . |
| 2,549,303 | 4/1949 | Friden . |
| 2,569,720 | 3/1949 | Jesnig . |
| 2,573,918 | 11/1949 | McCuiston . |
| 2,579,280 | 6/1949 | Trumbour et al. . |
| 2,581,182 | 3/1950 | Fields . |
| 2,587,215 | 4/1950 | Priestly . |
| 2,592,369 | 10/1950 | Young et al. . |
| 2,598,525 | 11/1950 | Fox . |
| 2,603,215 | 2/1951 | Arnow . |
| 2,603,216 | 6/1951 | Taplin et al. . |
| 2,604,094 | 6/1951 | Miller et al. . |
| 2,672,865 | 7/1951 | Willis . |
| 2,722,935 | 11/1955 | Thompson et al. . |
| 2,946,332 | 12/1957 | Sacks . |
| 2,992,645 | 3/1959 | Fowler . |
| 3,518,992 | 9/1967 | Altounyan et al. . |
| 3,635,219 | 1/1972 | Altounyan et al. . |
| 3,658,059 | 4/1972 | Steil . |
| 3,669,113 | 6/1972 | Altounyan et al. . |
| 3,795,244 | 3/1974 | Lax et al. . |
| 3,807,400 | 4/1974 | Cocozza . |
| 3,809,084 | 5/1974 | Hansen . |
| 3,837,341 | 9/1974 | Bell . |
| 3,858,583 | 1/1975 | Hallworth et al. . |
| 3,870,046 | 3/1975 | Elliott . |
| 3,888,253 | 6/1975 | Watt et al. . |
| 3,897,779 | 8/1975 | Hansen . |
| 3,906,950 | 9/1975 | Cocozza . |
| 3,921,637 | 11/1975 | Bennie et al. . |
| 3,948,264 | 4/1976 | Wilke et al. . |
| 3,949,751 | 4/1976 | Birch et al. . |
| 3,964,483 | 6/1976 | Mathes . |
| 3,971,377 | 7/1976 | Damani . |
| 3,973,566 | 8/1976 | Mathes . |
| 3,980,074 | 9/1976 | Watt et al. . |
| 3,991,761 | 11/1976 | Cocozza . |
| 4,013,075 | 3/1977 | Cocozza . |
| 4,014,336 | 3/1977 | Mathes . |
| 4,047,525 | 9/1977 | Kulessa et al. . |
| 4,064,878 | 12/1977 | Lundquist . |
| 4,069,819 | 1/1978 | Valentini et al. . |
| 4,098,273 | 7/1978 | Glenn . |
| 4,105,027 | 8/1978 | Lundquist . |
| 4,116,195 | 9/1978 | James . |
| 4,117,844 | 10/1978 | James . |
| 4,147,166 | 4/1979 | Hansen . |
| 4,192,309 | 3/1980 | Poulsen .................... 128/203.15 |
| 4,200,099 | 4/1980 | Guenzel et al. . |
| 4,206,758 | 6/1980 | Hallworth et al. ............ 128/203.15 |
| 4,227,522 | 10/1980 | Carris .................... 128/203.15 |
| 4,249,526 | 2/1981 | Dean et al. ................ 128/203.15 |
| 4,307,734 | 12/1981 | Blankenship ................ 131/329 |
| 4,338,931 | 7/1982 | Cavazza .................... 128/203.15 |
| 4,353,365 | 10/1982 | Hallworth et al. ............ 128/203.15 |

(List continued on next page.)

Primary Examiner—Edgar S. Burr
Assistant Examiner—Kimberly L. Asher
Attorney, Agent, or Firm—Richard E. Jenkins

[57] ABSTRACT

A breath actuated inhalator having a primary and a secondary air flow conduit wherein regulator means are provided in the secondary air flow conduit to planate maximum air flow velocity through the inhaler. By optimizing air flow and velocity rate, the breath actuated inhalator prevents problems associated with excessive inhalation velocity such as dry powder drug compound impingement upon the outside radius of the throat.

22 Claims, 6 Drawing Sheets

U.S. PATENT DOCUMENTS

| | | | |
|---|---|---|---|
| 4,423,724 | 1/1984 | Young | 128/203.15 |
| 4,446,862 | 5/1984 | Baum et al. | 128/203.15 |
| 4,524,769 | 6/1985 | Wetterlin | 128/203.15 |
| 4,570,630 | 2/1986 | Elliott et al. | 128/203.15 |
| 4,620,847 | 11/1986 | Shishov et al. | 604/58 |
| 4,627,432 | 12/1986 | Newell et al. | 128/203.15 |
| 4,664,107 | 5/1987 | Wass | 128/200.23 |
| 4,667,668 | 5/1987 | Wetterlin | 128/203.15 |
| 4,668,218 | 5/1987 | Virtanen | 604/58 |
| 4,739,754 | 4/1988 | Shaner | 128/203.23 |
| 4,803,978 | 2/1989 | Johnson, IV et al. | 128/200.23 |
| 4,811,731 | 3/1989 | Newell et al. | 128/203.15 |
| 4,841,964 | 6/1989 | Hurka et al. | 128/203.15 |
| 4,846,168 | 7/1989 | Abiko et al. | 128/203.15 |
| 4,884,565 | 12/1989 | Cocozza | 128/203.21 |
| 4,889,114 | 12/1989 | Kladders | 128/203.15 |
| 4,907,583 | 3/1990 | Wetterlin et al. | 128/203.15 |

DOSAGE INHALATOR WITH AIR FLOW VELOCITY REGULATING MEANS

TECHNICAL FIELD

This invention relates to breath actuated inhalers for the administration of a dose of medicament in powder form.

RELATED ART

There are essentially two classes of inhalation devices currently being offered in the marketplace for bronchial administration of a dose of dry powder medicament. The predominant inhalation device is a pressurized aerosol inhaler which discharges a metered dose of medication suspended in a pharmaceutically inert liquid propellant, e.g., a fluorocarbon.

These propelled inhalation devices have the property of consistently delivering a predetermined dose of medication. However, the particles of medication are propelled at a high velocity from the metering valve, and some of the medication is deposited on the back of the mouth and in the throat of the patient. Thus, while a consistent, metered dose leaves the valve of the device, the effective dose entering the lungs can vary with the shape and physical dimensions of the patient's oral cavity and his ability to coordinate his breathing with the discharge of the medication.

A second class of inhalation devices known to Applicant and existing in the marketplace utilize the patient's inhaled breath as a vehicle to transport the dry powder drug. However, these devices also presently suffer certain shortcomings which are well known to one skilled in the art. A primary shortcoming of the second class of inhalation devices is a lack of an air flow velocity regulating means which can result in excessive inhalation velocity during use of the devices. As with the propelled device, the excessive inhalation velocity can cause the dry powder drug being inhaled to impinge upon the back of the mouth and the throat and to be thwarted from completing the desired journey to the lungs. Applicant is not aware of a multi-dose inhaler for dry powder medicament which successfully serves to release the drug at an optimum air flow velocity rate so as to solve the aforementioned throat impingement difficulties. Quite to the contrary, the existing inhalation devices in the marketplace simply serve to introduce a dosage of a dry powder medicament into an air conduit without any control over the air flow transporting the medicament through the air conduit and to the patient's lungs. Thus, a need exists for a multi-dose dry powder inhaler that is easy to use by the patient and that does not demand coordination between actuation and inhalation.

Representative of presently known dry powder inhalation devices is the TURBUHALER ® which is marketed by AB Astra in Europe and the subject matter of U.S. Pat. Nos. 4,524,769 and 4,907,583 (assigned to AB Draco of Sweden). This dry powder medicament inhaler device was developed for the delivery of small quantities of pharmacologically active dry powder compounds (for example, less than one milligram per actuation) without any carrier compound. The breath actuated inhaler comprises: a mouthpiece with inserts; a by-pass air inlet; an inhalation channel; an air inlet; a desiccant store; a storage unit for the drug compound; a dosing unit; an operating unit; and a turning grip. The dosing unit is constructed as a disk with groups of conical holes for the drug compound and is positioned at the bottom of the storage unit. The larger diameter bottom areas of the truncated cones of the disk face the storage unit so as to facilitate filling during the loading and emptying of the dosing unit at inhalation. Dosing is accomplished by rotating the dosing unit in the storage unit toward a pressure plate beneath the dosing unit. Plastic scrapers positioned over the dosing unit serve to load the holes with the drug compound, and dosing is performed by merely twisting the turning grip back and forth.

When a patient inhales through the inhaler, the air enters a channel in the operating unit and passes through a hole in the pressure plate and through the dosing unit for release of the dose loaded in certain conical holes exposed to the area of the inhalation channel. Dry powder drug aggregates are broken up or deaggregated by the turbulent air flow in the inhalation channel and by the inserts in the nozzle mouthpiece. The non-refill inhaler can provide up to 200 doses prior to disposal thereof.

As is well known in the inhalator art, however, this type of multiple dose inhaler suffers from a number of shortcomings including potentially significant dosage variability since the holes in the dosing unit disk are not always completely filled with the drug compound during dosing.

Another earlier concept for a multiple dose inhaler is disclosed in U.S. Pat. No. 2,587,215 to Priestly which discloses a device for the diffusion and inhalation of dry powder compounds such as penicillin and the like into the nasal and/or oral passages for the treatment of certain diseases and infections, particularly for the treatment of sinusitis and infections of the throat and lungs. As an improvement over earlier heavy and unattractive devices, the relatively small inhalator comprises a body and a supply chamber and a mixing chamber formed in the body. A spring-loaded slide means is provided to carry a predetermined amount of powder from the supply chamber to the mixing chamber, and a tube with a restricted end is positioned within the mixing chamber and extends therefrom to serve as an inhalation nozzle for a patient. Air passages provide air to the mixing chamber to mix the air and dry powder compound, and a secondary air opening is provided adjacent the restricted end of the tube in order to provide for further mixing of the air and dry powder compound as the compound is inhaled.

In use, the open end of the tube is placed in the nostril or mouth of a patient and a deep breath is then taken. The air entering the oral or nasal cavity is drawn through the primary air passages into the mixing chamber where it mixes with the powder so as to diffuse it and carry it into the tube. The restriction at the end of the tube causes a pressure drop therein so that air will enter through the secondary air opening adjacent the restricted end of the tube in order to facilitate further mixing of the air and dry powder compound. Finally, the diffused mixture is transported through the tube and to the oral or nasal cavities.

The dry powder compound is provided to the Priestly inhalator by means of a large size pharmacy capsule which is inserted into an opening in the inhalator body so as to provide for multiple dosing of the dry powder contained therein. Alternatively, the Priestly patent discloses that the inhalator of the invention could be used without a capsule merely by filling the supply chamber and covering it with a cap or by having the powder sealed in the supply chamber so as to provide a disposable inhaler.

The Priestly inhalator also suffers from a number of shortcomings and particularly an inability to provide a consistent air flow velocity during inhalation. This can result in coagulation of the drug during inhalation and/or in impingement of the drug upon the upper throat as will be appreciated by those familiar with the inhalator art.

The shortcomings of prior art dry powder medicament inhalators have now been overcome by the inhalator of the present invention which provides for a dosage inhalator with regulating means to provide a substantially constant predetermined maximum air flow velocity through the inhalator.

DISCLOSURE OF THE INVENTION

Therefore, in accordance with the present invention, Applicant provides a dosage inhalator with air flow velocity regulating means designed specifically to overcome known problems inherent with excessive inhalation velocity (for example, impingement of the dry powder compound upon the outside radius of the throat so as to thwart the desired journey to the patient's lungs). The dosage inhalator comprises a housing defining an air inlet end and an air exit end wherein the exit end includes a nozzle mouthpiece. A storage chamber is formed within the housing for storing a pharmacologically active dry powder compound to be dispensed by the inhalator. A primary air conduit defining a venturi therein is provided within the housing, and a secondary air conduit is further provided within the housing adjacent the primary air conduit.

Dose introduction means are provided within the housing for transporting a predetermined portion of the dry powder compound from the storage chamber to the primary air conduit and releasing the compound therein, and the dose introduction means is adapted to substantially close the primary air conduit to air flow prior to actuation thereof and to allow for air flow through the primary air conduit subsequent to actuation thereof. Finally, regulator means are positioned in the secondary air conduit for controlling air flow velocity therethrough wherein the regulator means normally close the secondary air conduit to air flow and are adapted to move between a first position wherein the secondary air conduit is substantially closed and a second position wherein the secondary air conduit is substantially open in response to air pressure differentials created in the venturi of the primary air conduit as a patient inhales through the nozzle mouthpiece of the inhalator. Thus, the regulator means acts to provide a substantially constant maximum air flow velocity through the inhalator by regulating the air flow through the secondary air conduit during inhalation.

It is therefore the object of this invention to provide an improved multi-dose dry powder inhalator.

It is another object of the present invention to provide an improved multi-dose dry powder inhalator which obviates dry powder inhalation problems due to excessive air flow velocity during inhalation.

It is yet another object of the present invention to provide an improved dry powder inhalator which includes regulator means to provide a constant maximum air flow velocity through the inhalator by regulating the air flow therethrough.

Some of the objects of the invention having been stated, other objects will become evident as the description proceeds, when taken in connection with the accompanying drawings.

BEST MODE FOR CARRYING OUT THE INVENTION

As used in the specification of the instant application, the term "propellant" means a pressurized gas for expelling the drug contents (dose) from a canister/valve assembly. The term "dry powder medicament" used herein means a dry powder substance used to achieve a therapeutic effect in respiratory therapy. The term "multi-dose dry powder inhalator" used herein means a device that is capable of delivering more than one dose without refilling the device. The term "planated air flow velocity" used herein means an air flow velocity that remains constant independent of mass flow rate, and the term "breathing profiles" used herein means the volume of air inhaled or exhaled as a function of time.

Referring now more specifically to the drawings, a preferred embodiment of a dry powder dosage inhalator according to the present invention is shown in FIGS. 1-6 and generally designated 10. Inhalator 10 comprises a housing 12 which is preferably formed from a plastic material although the housing may be made of any suitable material and is not limited to plastic. Housing 12 includes storage chamber 14 therein for storing a suitable amount of a selected dry powder pharmacologically active compound C for multiple dosing with inhalator 10. Storage chamber 14 is sealed with storage chamber cap 14A which is preferably an induction-sealed liner cap with a built-in desiccant (not shown) for moisture protection of the dry powder contained within storage chamber 14.

The portion of housing 12 through which air flows during inhalation includes primary air conduit P and secondary air conduit S as best seen in FIGS. 1-4. As will be appreciated with particular reference to FIGS. 1 and 2, primary air conduit P defines a venturi therein which creates lower air pressure in the medial area thereof when the conduit is open and air flow is occurring therethrough. The venturi within primary air conduit P is formed between housing wall portion 12A and housing wall portion 12B as best appreciated with reference to FIGS. 1 and 2.

An air flow maximum velocity regulator 16 is positioned within secondary air conduit S in order to achieve a planated discharge air flow velocity from the nozzle mouthpiece 18 of housing 12. Air flow velocity regulator 16 comprises a diaphragm 16A which is urged into a normally open position by a suitable internal spring element (not shown) so as to maintain secondary air conduit S normally closed to air flow. Diaphragm 16A is pivotably mounted to housing wall portion 12B and includes air flow regulator plate 16B which serves to maintain secondary air conduit S in a normally closed position by contacting housing wall portion 12C (as best seen with reference to FIGS. 1 and 2). Upon inhalation by a patient (as will be described in detail hereinafter) regulator plate 16B will be urged away from contact with housing wall portion 12C and toward housing wall portion 12B so as to open secondary air conduit S to air flow.

Figure 1:
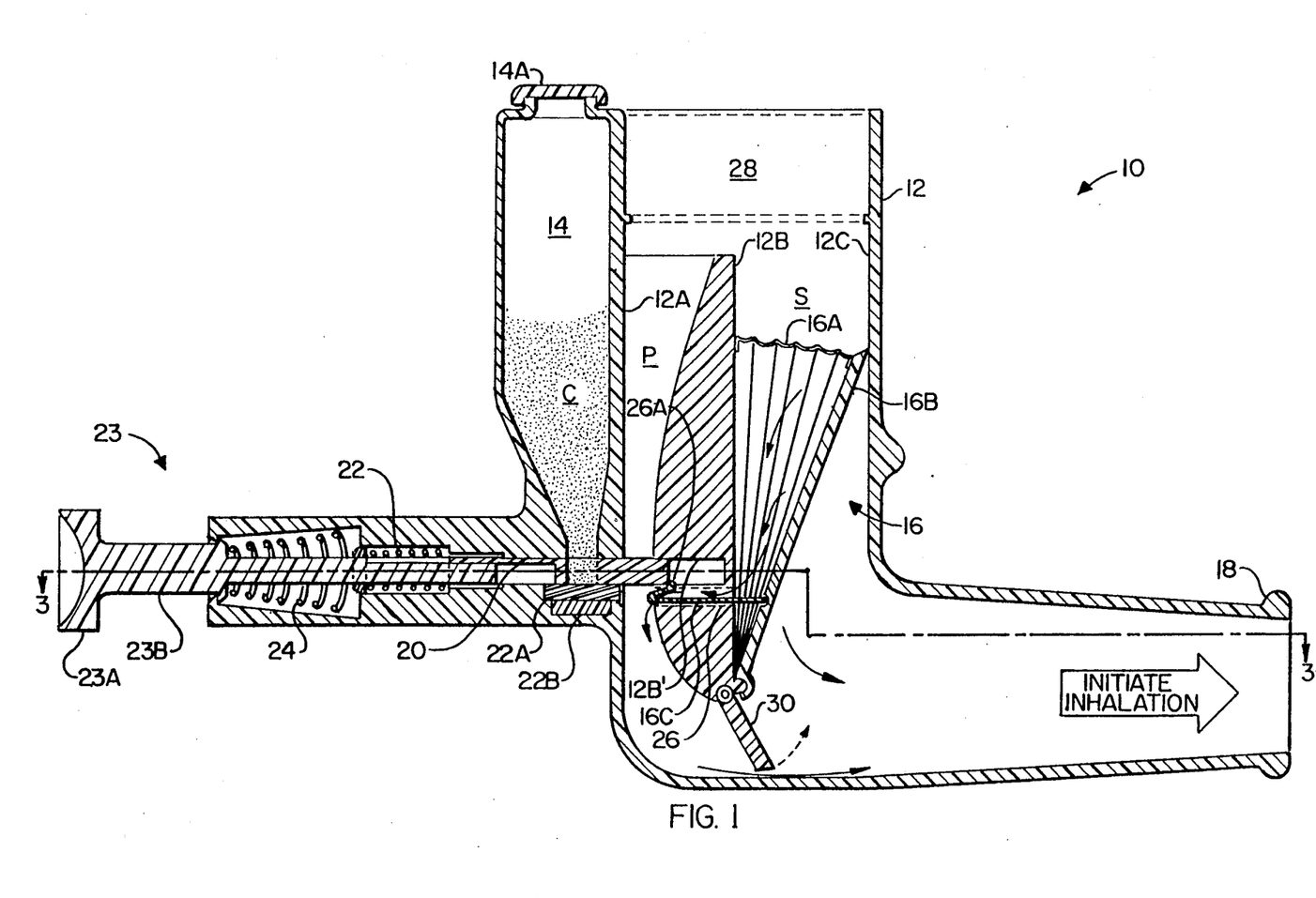
FIG. 1 is a vertical cross sectional view of the inhalator of the invention prior to actuation thereof.
Figure 2:
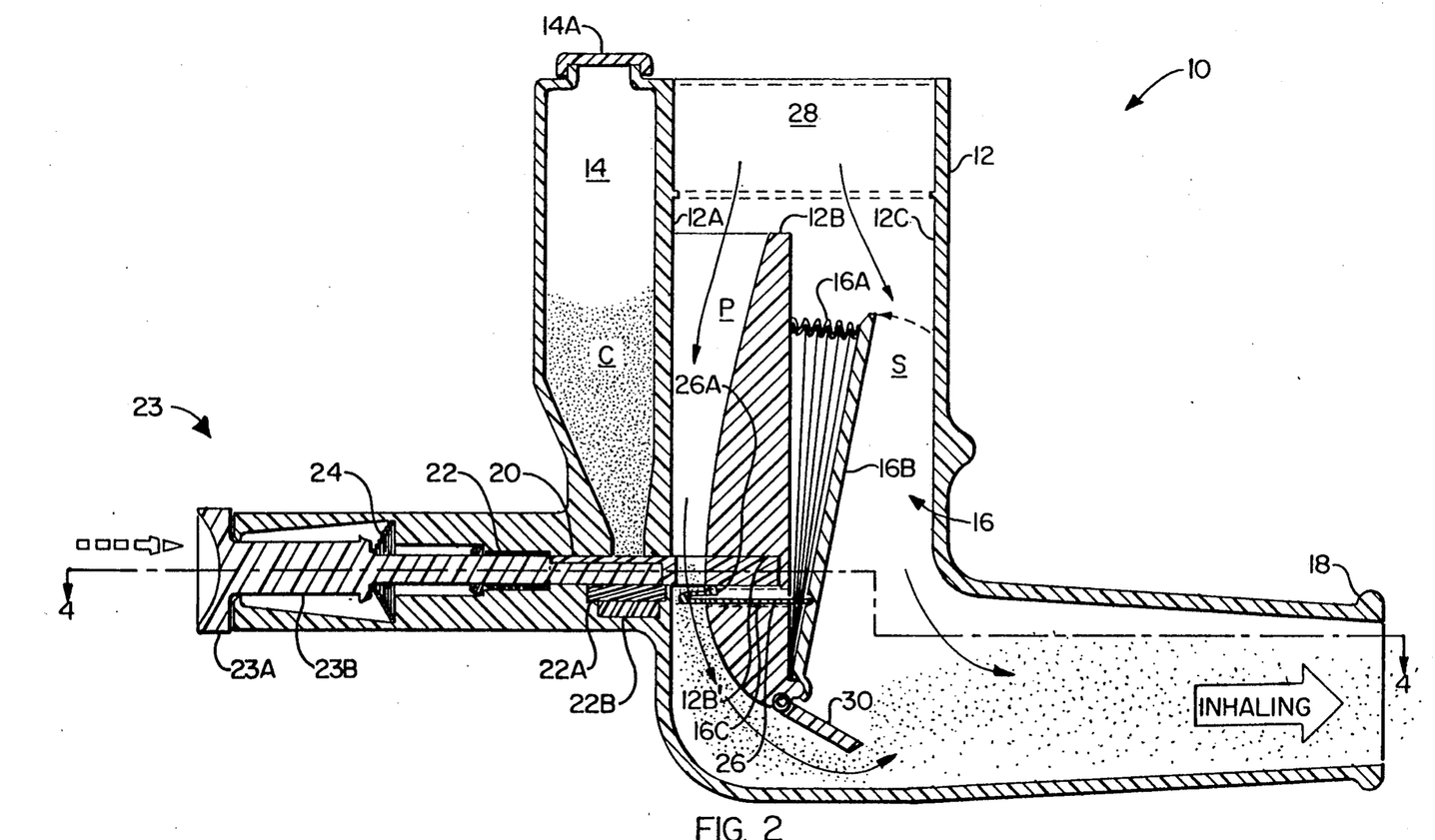
FIG. 2 is a vertical cross sectional view of the inhalator of the invention subsequent to actuation thereof.
Figure 3:
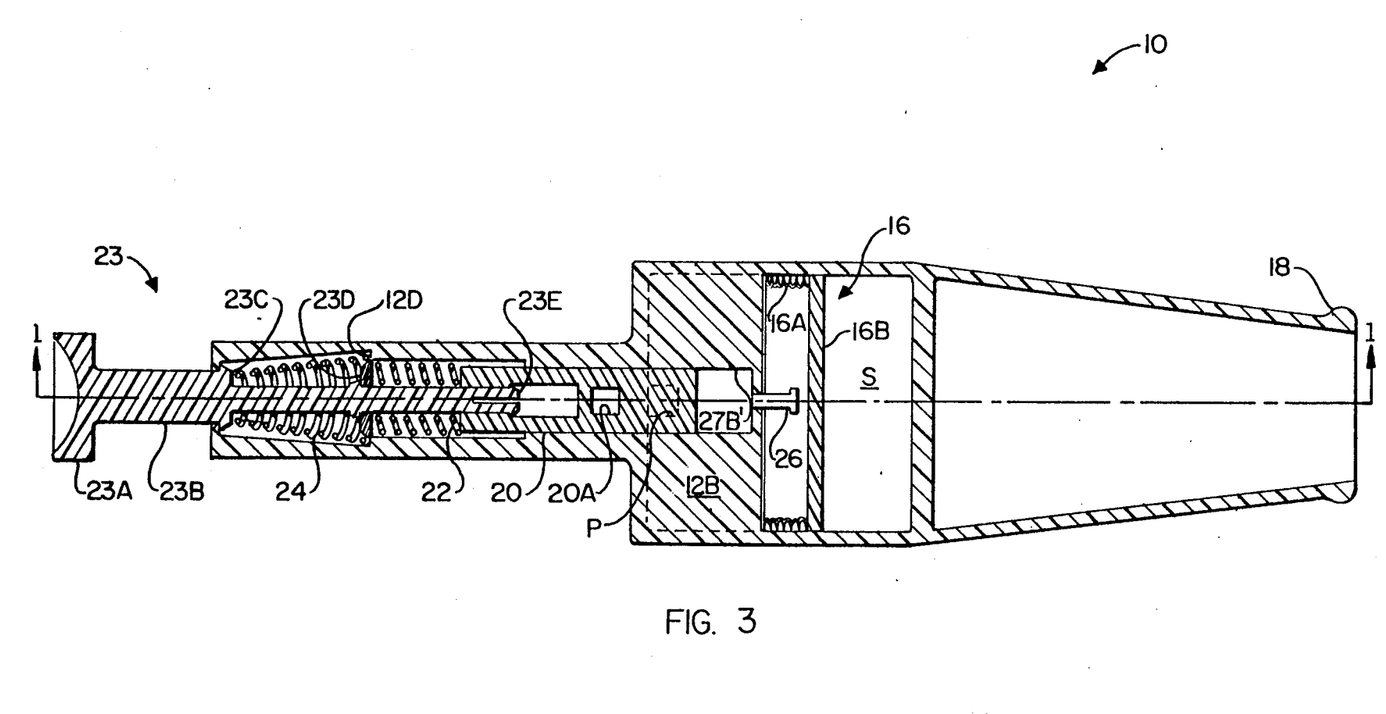
FIG. 3 is a horizontal cross sectional view of the inhalator of the invention taken on line 3—3 of FIG. 1.
Figure 4:
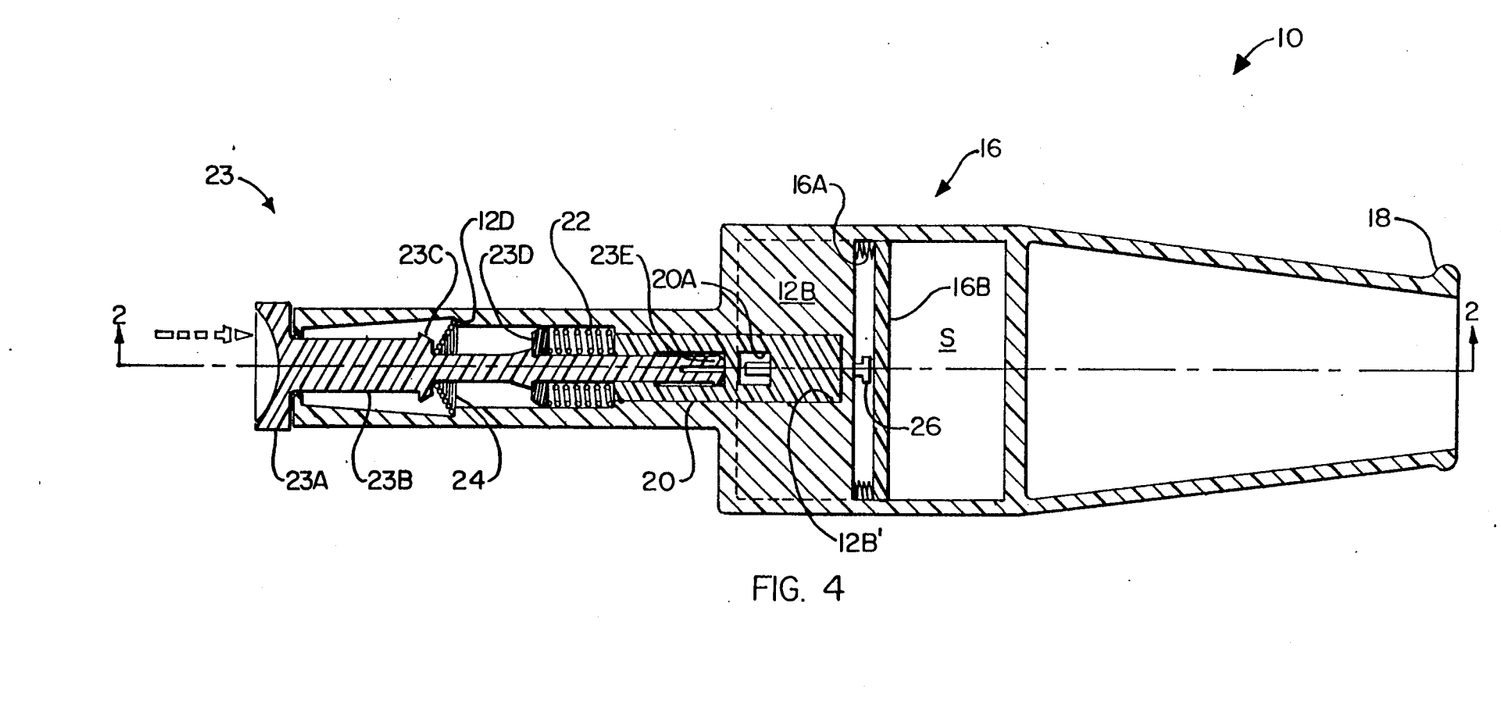
FIG. 4 is a horizontal cross sectional view of the inhalator of the invention taken on line 4—4 of FIG. 2.
Figure 5:
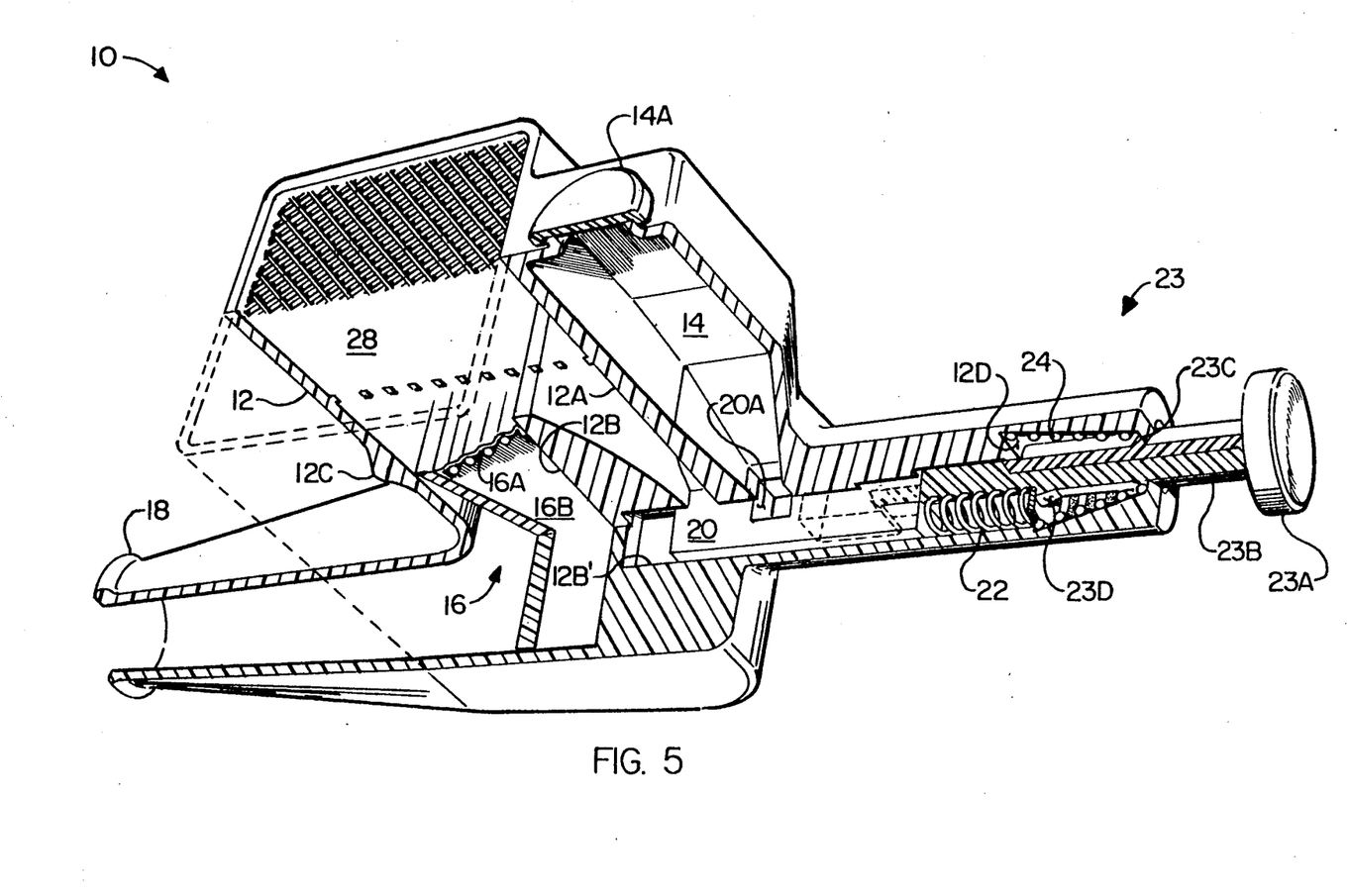
FIG. 5 is a perspective view with parts broken away of the inhalator of the invention prior to actuation thereof.
Figure 6:
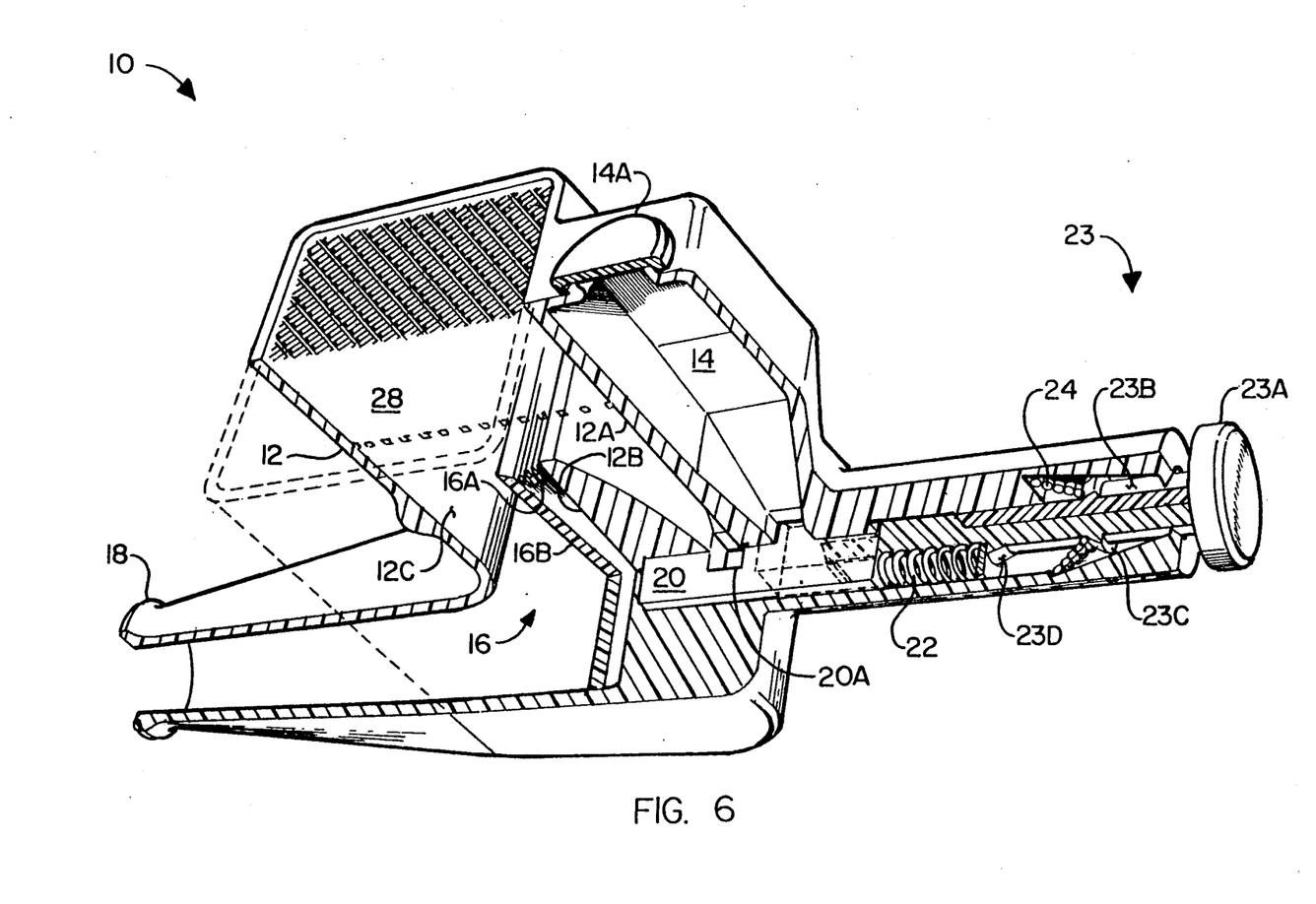
FIG. 6 is a perspective view with parts broken away of the inhalator of the invention subsequent to actuation thereof.

A predetermined charge of dry powder compound C is delivered from storage chamber 14 to primary air conduit P by metering plate 20 which can best be understood with reference to FIGS. 1–4. Metering plate 20 is slidably mounted within housing 12 of inhalator 10 so as to be normally retained in a first position wherein dry powder receiving aperture 20A is located adjacent the open bottom of storage chamber 14. Metering plate 20 is further adapted to be slidably urged by metering plate preload spring 22 to a second position wherein aperture 20A is positioned within primary air conduit P so as to discharge the metered dose of dry powder C into the air flow within primary air conduit P. Also, and very importantly, it should be observed that the front portion of metering plate 20 serves to substantially close primary air conduit P when the metering plate is in the first position and to render primary air conduit P open to air flow through aperture 20A when metering plate 20 is in the previously described second position.

With reference again to FIGS. 1–4, the spring mechanism for urging metering plate 20 from the first to the second position will be described in detail. An actuator 23 comprising an actuator button 23A and an actuator stem 23B (defining three annular rings along the length thereof consisting of first annular ring 23C, second annular ring 23D and third annular ring 23E) serves to apply a resilient force against the outermost end of metering plate 20 when button 23A is depressed. This acts to slide actuator stem 23B inwardly which serves to: (1) urge second annular ring 23D inwardly so as to compress metering plate preload spring 22 tightly against metering plate 20; and (2) urge actuator return spring 24 inwardly against shoulder 12D defined within housing 12 by means of first annular ring 23C so that actuator 23 will be urged to return to its original position when released. Thus, pressing actuator 23 inwardly serves to compress metering plate preload spring 22 to a known force which is independent of the force applied to actuator button 23A so long as the button is fully depressed and maintained in that position.

Once actuator button 23A is fully depressed so as to compress metering plate preload spring 22 against the end of metering plate 20, metering plate 20 is released so as to travel from the aforementioned first position to the second position by initiating inhalation on nozzle mouthpiece 18. The inhalation serves to create a vacuum or pressure differential downstream of both metering plate 20 in primary air conduit P and air flow velocity regulator 16 in secondary air conduit S. The partial vacuum or pressure differential serves to withdraw air from diaphragm 16A through fluidly communicating passage 16C (defined by housing wall portion 12B) and into the throat of the venturi defined within primary air conduit P. The withdrawal of air from diaphragm 16A serves to accomplish two purposes: (1) diaphram 16A contracts so as to open secondary air conduit S; and (2) metering plate release pin 26, pivotably mounted to regulator plate 16B, is slidably motivated so as to depress detent 26A at the remote end thereof which normally retains metering plate 20 in the first position. This serves to release metering plate 20 to allow it to be slidably urged to its second position wherein aperture 20A thereof introduces a dry powder compound dosage into primary air conduit P and opens the air conduit for air flow therethrough. As can be best appreciated with reference to FIGS. 1–2 and 5–6, the innermost end of metering plate 20 is allowed to move from the first position to the second position by the innermost end thereof being slidably received within slot 12B′ of housing wall portion 12B. With both primary air conduit P and secondary air conduit S now both open to air flow therethrough, regulator plate 16B of air flow velocity regulator 16 is contracted and released in accordance with the partial vacuums or air pressure differentials created in the venturi of primary air conduit P so as to planate the total air flow through inhalator 10 during inhalation. Velocity regulator 16 acts as part of a closed loop feedback system with the venturi of primary air conduit P serving as the flow measurement device.

By way of further explanation, a predetermined maximum air flow velocity is maintained since if air flow velocity tends to become too high in primary air conduit P a pressure differential or partial vacuum will be created in the venturi which will serve to further contract diaphragm 16A and thereby further open secondary air conduit S to air flow which acts to decrease air flow velocity at nozzle mouthpiece 18. If the air flow velocity through primary air conduit P becomes relatively slow, the pressure differential or partial vacuum created in the venturi adjacent passage 16C will diminish and allow regulator plate 16B to be urged outwardly by diaphragm 16A to initiate closing of secondary air conduit S which acts to increase the air flow velocity at nozzle mouthpiece 18. In this fashion, inhalator 10 eliminates the need for physicians to train patients on breathing profiles since maximum air flow velocity is maintained due to the regulated air flow velocity through secondary air conduit S which can be designed to accommodate virtually any inhalation profile and thereby to minimize upper throat impingement of dry powder compound C.

Referring again to the drawings, additional features of inhalator 10 will now be described. Although not essential to the invention, preferably a desiccant 28 is provided at the top of housing 12 to ensure that incoming air is suitably dehumidified prior to passing through primary air conduit P and secondary air conduit S. Also, a pivotably mounted non-return valve 30 is provided at the base of housing wall portion 12B to protect against coughs or other circumstances which might create a reverse air flow through inhalator 10. Metering plate 20 is designed to render a zero clearance seal to storage chamber 14 in order to prevent moisture penetration with a metering plate bearing assembly comprising plastic bearing 22A urged against metering plate 20 by resilient polymeric element 22B which serves as a preloading spring therebeneath to urge the metering plate against the bottom aperture of storage chamber 14.

Finally, as best seen in FIGS. 1–4, when actuator button 23A has been held in a depressed position and a predetermined dose of dry powder compound C is inhaled by a patient through nozzle mouthpiece 18, actuator button 23A is released and urged outwardly by actuator return spring 24. As actuator stem 22B is slidably urged outwardly from housing 12, third annular ring 23E serves to engage metering plate 20 and to withdraw it to its first position. As metering plate 20 is slidably moved from its second dosage introduction position to its first dosage loading position, detent 26A at the free end of metering plate release pin 26 is released and again engages the innermost or front end of metering plate 20 so as to maintain it in its first position until actuator 22 is again depressed by the patient in order to administer a dosage of dry powder compound C.

In use, a patient presses actuator button 23A which compresses metering plate preload spring 22 to a known force which is independent of the loading on the actuator button as long as the button is fully depressed. As the patient inhales through the nozzle mouthpiece 18 of inhalator 10, a pressure differential is set up across the venturi throat defined within primary air conduit P since both primary air conduit P and secondary air conduit S are closed. At a preset pressure differential or partial vacuum, air flow velocity regulator 16 begins to open and simultaneously actuate metering plate release pin 26 which releases metering plate 20. Metering plate 20 is urged from its first position to its second position by metering plate preload spring 22 and thereby discharges the predetermined metered dose of dry powder pharmacologically active compound C into the air flow staged in primary air conduit P by the aforementioned pressure differential. Diaphragm 16A serves to continue to contract and expand so as to open and close, respectively, secondary air conduit S in order to planate the total air flow through inhalator 10 by acting as a closed loop feedback system with the venturi serving as the air flow measurement device therefor.

Among the dry powder medicaments which are suitable for administering with the dosage inhalator of the present invention are those currently administered by inhalation such as $\beta_2$-stimulants ($\beta_2$-agonist), anticholinergic drugs, corticosteriods, antiallergic drugs and miscellaneous drugs used to treat respiratory disorders. For example, $\beta_2$-stimulants include, but are not limited to, albuterol, salmeterol, fenoterol, pirbuterol, reproterol, imiterol, terbutalline, tulobuterol, isoprenaline and oxaprenaline; anticholinergic drugs include, but are not limited to, ipratropium bromide and oxitropium bromide; corticosteriods include, but are not limited to, fluticasone propionate and beclomethasone dipropionate; antiallergic drugs include, but are not limited to, sodium cromglycate, ketotifen and nedocromil sodium; and miscellaneous drugs include, but are not limited to, amiloride.

It will thus be seen that there has been described above a dual air flow conduit breath actuated multi-dose inhalator which is designed to utilize bulk dry powder compound and wherein the dry powder compound discharge air flow velocity is planated by an air flow regulated secondary air conduit.

It will be understood that various details of the invention may be changed without departing from the scope of the invention. Furthermore, the foregoing description is for the purpose of illustration only and not for the purpose of limitation—the invention being defined by the claims.

What is claimed is:

1. A portable dosage inhalator for dispensing to a patient a predetermined amount of a pharmacologically active dry powder compound, comprising:

a housing defining an air inlet end, said air exit end comprising a nozzle for insertion into the mouth of a patient;

a storage chamber formed within said housing for storing said compound to be dispensed by said inhalator;

a primary air conduit within said housing and defining a venturi therein;

a secondary air conduit within said housing adjacent said primary air conduit;

dose introduction means provided within said housing for transporting a predetermined portion of said compound from said storage chamber to said primary air conduit and releasing said compound therein, said dose introduction means adapted to substantially close said primary air conduit to air flow prior to actuation thereof and to allow for air flow through said primary air conduit subsequent to actuation thereof; and regulator means positioned in said secondary air conduit for controlling air flow velocity therethrough, said regulator means normally closing said secondary air conduit to air flow and adapted to move between a first position wherein said secondary air conduit is substantially closed and a second position wherein said secondary air conduit is substantially open in response to air pressure differentials created in the venturi of said primary air conduit as a patient inhales through the nozzle of said air exit end of said housing;

whereby said regulator means acts to provide a substantially constant maximum air flow velocity through said inhalator by regulating the air flow through said secondary air conduit during inhalation by a patient.

2. A portable dosage inhalator according to claim 1 wherein said dose introduction means comprises a slide element extending across the bottom of said storage chamber and traversing the venturi of said primary air conduit prior to actuation thereof, said slide element defining a compound receiving aperture therethrough in the portion positioned beneath said storage chamber prior to actuation thereof.

3. A portable dosage inhalator according to claim 2 wherein said slide element comprises spring means for resiliently urging said slide from said storage chamber to said primary air conduit upon actuation thereof.

4. A portable dosage inhalator according to claim 1 wherein said regulator means comprises a normally open diaphragm positioned in said secondary air conduit and in fluid communication with the venturi of said primary air conduit, said diaphragm being adapted to contract and thereby open said secondary air conduit to air flow in response to low pressure in the venturi of said primary air conduit.

5. A portable dosage inhalator according to claim 1 including actuation means operatively connecting said regulator means and said dose introduction means for actuating said dose introduction means when said regulator means first moves from said normally closed first position toward said second position.

6. A portable dosage inhalator according to claim 5 wherein said actuation means comprises a link mounted at one end to said regulator means and the other end thereof adapted to releasably engage said dose introduction means.

7. A portable dosage inhalator according to claim 1 wherein said housing includes a desiccant in said air inlet end.

8. A portable dosage inhalator according to claim 1 including a non-return valve mounted between said primary air conduit and the nozzle of said inhalator to prevent reverse air flow.

9. A portable dosage inhalator for dispensing to a patient a predetermined amount of a pharmacologically active dry powder compound, comprising:
a housing defining an air inlet end and an air exit end, said air exit end comprising a nozzle for insertion into the mouth of a patient;
a storage chamber formed within said housing for storing said compound to be dispensed by said inhalator;
air conduit within said housing and defining a venturi therein;
a secondary air conduit within said housing adjacent said primary air conduit;
dose introduction for transporting a predetermined portion of said compound from said storage chamber to said primary air conduit and releasing said compound therein, said dose introduction means adapted to substantially close said primary air conduit to air flow prior to actuation thereof and to allow for air flow through said primary air conduit subsequent to actuation thereof;
regulator means positioned in said secondary air conduit for controlling air flow velocity therethrough, said regulator means normally closing said secondary air conduit to air flow and adapted to move between a first position wherein said secondary air conduit is substantially closed and a second position wherein said secondary air conduit is substantially open in response to air pressure differentials created in the venturi of said primary air conduit as a patient inhales through the nozzle of said air exit end of said housing; and
actuation means operatively connecting said regulator means and said dose introduction means for actuating said dose introduction means when said regulator means first moves from said normally closed first position toward said second position;
whereby said regulator means acts to provide a substantially constant maximum air flow velocity through said inhalator by regulating the air flow through said secondary air conduit during inhalation by a patient.

10. A portable dosage inhalator according to claim 9 wherein said dose introduction means comprises a slide element extending across the bottom of said storage chamber and traversing the venturi of said primary air conduit prior to actuation thereof, said slide element defining a compound receiving aperture therethrough in the portion positioned beneath said storage chamber prior to actuation thereof.

11. A portable dosage inhalator according to claim 10 wherein said slide element comprises spring means for resiliently urging said slide from said storage chamber to said primary air conduit upon actuation thereof.

12. A portable dosage inhalator according to claim 9 wherein said regulator means comprises a normally open diaphragm positioned in said secondary air conduit and in fluid communication with the venturi of said primary air conduit, said diaphragm being adapted to contract and thereby open said secondary air conduit to air flow in response to low pressure in the venturi of said primary air conduit.

13. A portable dosage inhalator according to claim 9 wherein said actuation means comprises a link mounted at one end to said regulator means and the other end thereof adapted to releasably engage said dose introduction means.

14. A portable dosage inhalator according to claim 9 wherein said housing includes a desiccant in said air inlet end.

15. A portable dosage inhalator according to claim 9, including a non-return valve mounted between said primary air conduit and the nozzle of said inhalator to prevent reverse air flow.

16. A portable dosage inhalator for dispensing to a patient a predetermined amount of a pharmacologically active dry powder compound, comprising:
a housing defining an air inlet end and an air exit end, said air exit end comprising a nozzle for insertion into the mouth of a patient;
storing said compound to be dispensed by said inhalator;
a primary air conduit within said housing and defining a venturi therein;
a secondary air conduit said primary air conduit;
dose introduction means provided within said housing for transporting a predetermined portion of said compound from said storage chamber to said primary air conduit and releasing said compound therein, said dose introduction means adapted to substantially close said primary air conduit to air flow prior to actuation thereof and to allow for air flow through said primary air conduit subsequent to actuation thereof;
a normally open diaphragm positioned ins aid secondary air conduit and in fluid communication with the venturi of said primary air conduit for controlling air flow velocity therethrough, said diaphragm normally closing said secondary air conduit to air flow and adapted to contract and thereby to move between a first position wherein said secondary air conduit is substantially closed and a second position wherein said secondary air conduit is substantially open in response to air pressure differentials created in the venturi of said primary air conduit as a patient inhales through the nozzle of said air exit end of said housing; and
actuation means operatively connecting said regulator means and said dose introduction means for actuating said dose introduction means when said regulator means first moves from said normally closed first position toward said second position;
whereby said diaphragm acts to provide a substantially constant maximum air flow velocity through said inhalator by regulating the air flow through said secondary air conduit during inhalation by a patient.

17. A portable dosage inhalator according to claim 16 wherein said dose introduction means comprises a slide element extending across the bottom of said storage chamber and traversing the venturi of said primary air conduit prior to actuation thereof, said slide element defining a compound receiving aperture therethrough in the portion positioned beneath said storage chamber prior to actuation thereof.

18. A portable dosage inhalator according to claim 17 wherein said slide element comprises spring means for resiliently urging said slide from said storage chamber to said primary air conduit upon actuation thereof.

19. A portable dosage inhalator according to claim 16 wherein said actuation means comprises a link mounted at one end to said diaphragm and the other end thereof adapted to releasably engage said dose introduction means.

20. A portable dosage inhalator according to claim 19 wherein an air passageway extends between said diaphragm and said primary air conduit to provide fluid communication therebetween, and said link operatively connecting said regulator means and said dose introduction means extends therethrough.

21. A portable dosage inhalator according to claim 16 wherein said housing includes a desiccant in said air inlet end.

22. A portable dosage inhalator according to claim 16 including a non-return valve mounted between said primary air conduit and the nozzle of said inhalator to prevent reverse air flow.

* * * * *